(12) United States Patent
Marchini et al.

(10) Patent No.: US 9,592,260 B2
(45) Date of Patent: Mar. 14, 2017

(54) CANCER THERAPY WITH A PARVOVIRUS COMBINED WITH AN HDAC INHIBITOR

(71) Applicant: Deutsches Krebsforschungszentrum, Heidelberg (DE)

(72) Inventors: Antonio Marchini, Heidelberg (DE); Jean Rommelaere, Heidelberg (DE); Nazim El-Andaloussi, Heidelberg (DE); Georgi Hristov, Heidelberg (DE); Junwei Li, Eppelheim (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 31 days.

(21) Appl. No.: 14/507,160

(22) Filed: Oct. 6, 2014

(65) Prior Publication Data
US 2015/0030567 A1 Jan. 29, 2015

Related U.S. Application Data (62) Division of application No. 13/635,162, filed as application No. PCT/EP2011/001328 on Mar. 17, 2011, now abandoned.

(30) Foreign Application Priority Data

Mar. 17, 2010 (EP) .................................... 10002829

(51) Int. Cl.
*A61K 35/76* (2015.01)
*A61K 35/768* (2015.01)
*A61K 31/165* (2006.01)
*A61K 31/19* (2006.01)
*A61K 45/06* (2006.01)

(52) U.S. Cl.
CPC ............ *A61K 35/76* (2013.01); *A61K 31/165* (2013.01); *A61K 31/19* (2013.01); *A61K 35/768* (2013.01); *A61K 45/06* (2013.01); *C12N 2750/14332* (2013.01)

(58) Field of Classification Search
None
See application file for complete search history.

(56) References Cited

U.S. PATENT DOCUMENTS

2004/0220124 A1 11/2004 Rommelaere et al.
2009/0035292 A1 2/2009 Kovach et al.

FOREIGN PATENT DOCUMENTS

| WO | WO 2006/066133 A2 | 6/2006 |
| WO | WO 2006/075165 A1 | 7/2006 |
| WO | WO 2008/047138 A2 | 4/2008 |
| WO | WO 2009/083232 A1 | 7/2008 |

OTHER PUBLICATIONS

Angelova et al. Improvement of Gemcitabine-BasedTherapy of Pancreatic Carcinoma byMeans of Oncolytic Parvovirus H-1PV. Clin Cancer Res 2009; 15(2): 511-519.*
International Search Report dated May 23, 2011.
Li et al. Valproic acid induces growth arrest, apoptosis, and senescence in medulloblastomas by increasing histone hyperacetylation and regulating expression of p21Cip1, CDK4, and CMYC. Mol Cancer Ther 2005;4(12): 1912-22.
Liu et al. Trichostatin A and Oncolytic HSV Combination Therapy Shows Enhanced Antitumoral and Antiangiogenic Effects. Mol Ther. Jun. 2008 : 16(6): 1041-1047.
Watanabe et al. Histone deacetylase inhibitor FR901228 enhances the antitumor effect of telomerase-specific replication-selective adenoviral agent OBP-301 in human lung cancer cells. Experimental Cell Research 312 (2006) 256-265.
Junwei Li et al., Synergistic combination of valproic acid and oncolytic parvovirus H-1PV as a potential therapy against cervical and pancreatic carcinomas, EMBO Mol Med (2013) 5, 1537-1555.

* cited by examiner

*Primary Examiner* — Nick Zou
(74) *Attorney, Agent, or Firm* — Crowell & Moring LLP (57) ABSTRACT

Described is a pharmaceutical composition comprising (a) a parvovirus and (b) a histone deacetylase inhibitor (HDACI) and the use of said composition for treatment of cancer, e.g., brain tumor, cervical carcinoma, or pancreatic carcinoma.

3 Claims, 7 Drawing Sheets

Sub-G1 apoptotic cell population: CxCa

CANCER THERAPY WITH A PARVOVIRUS COMBINED WITH AN HDAC INHIBITOR

This application is a divisional of U.S. application Ser. No. 13/635,162 filed Mar. 17, 2011, which is a 371 of International Application No. PCT/EP2011/001328, filed Mar. 17, 2011, which claims priority from European Patent Convention Application No. 10002829.9, filed on Mar. 17, 2010, the disclosures of which are expressly incorporated by reference herein.

The present invention relates to a pharmaceutical composition comprising (a) a parvovirus and (b) a histone deacetylase inhibitor (HDACI) and the use of said composition for treatment of cancer, e.g., brain tumors, cervical carcinoma, or pancreatic carcinoma.

Cervical carcinoma is the second most frequent malignancy of women worldwide and is responsible of more than 270,000 deaths and 500,000 new cases every year. Certain types of human papillomaviruses (HPVs), so-called high risk types (e.g. types 16 and 18) are the causative agents of cervical carcinogenesis. Two viral oncogenes from the high risk HPVs, E6 and E7, are responsible for the malignant conversion of the cell and their continuous expression is associated with inactivation of cellular death pathways that are normally activated by genotoxic agents or soluble death ligands. Conventional treatment by radiotherapy, chemotherapy and surgery remains largely ineffective against HPV-associated carcinomas, and new therapeutic strategies are urgently needed. The recent launch of prophylactic vaccines, while giving hopes of achieving an efficient prevention of infection through vaccination, will require several decades before translating into a decrease of cervical cancer incidence.

Pancreatic ductal adenocarcinoma (PDAC) is one of the most lethal gastrointestinal malignancies. PDAC is the fourth most frequent cause of cancer-related deaths in North America, the sixth in Europe, and the fifth in the UK. The disease is highly resistant to currently available treatments. Surgical resection provides the best possibility for long-term survival, but is feasible in a minority of patients only and is not without risk. In advanced disease where surgery is not an option, chemotherapy comes into play, using in particular gemcitabine or 5-FU (5-fluorouracil), although the effects are still modest and always accompanied by high general toxicity. Gemcitabine has been approved by the FDA as a first line therapy for patients with locally advanced or metastatic pancreatic cancer. This drug is a cell-cycle dependent deoxycytidine analogue of the antimetabolite class, that is transported into cells through human equilibrative nucleoside transporters (hENT), and is phosphorylated to its active triphosphate form by deoxycitidine kinase (dCK). An important concern of gemcitabine therapy lies in the development of resistance towards this chemotherapeutic. This resistance can be due to reduced import/phosphorylation of the drug, and/or enhanced export from the cell by means of the ABC transporters family members MDR and MRP1/2, resulting in the depletion of the intracellular pool of activated gemcitabine. Combinations of gemcitabine with other therapeutic regimens are explored to either improve the anticancer effect by eradicating resistant variants or to allow for reduction of the doses of chemotherapy and its ensuing toxicity.

Several members of the rodent parvovirus group, including the rat parvovirus H-1PV and its mouse homolog minute virus of mice (MVM) have attracted high attention for their anticancer potential. Indeed, these viruses are nonpathogenic for humans and possess intrinsic oncolytic and oncosuppressive properties. Additionally, the fact that the human population has not been pre-exposed to H-1PV infection indicates that the problem of preexisting anti-viral immunity, a common reason for the low efficacy of virus based treatments, does not exist in the case of H-1PV. Therefore, the virus is not immediately cleared by the immune system of the patient after administration, increasing the effective time for the treatment.

The parvovirus genome consists of a single strand DNA of approximately 5100 bases containing two promoters, P4 and P38 which regulate the expression of the non structural (NS1 and NS2) and capsid (VP1 and VP2) proteins, respectively. Rodent parvoviruses have been shown to activate several death pathways. In particular, depending on cell type and growth conditions, H-1PV is able to induce apoptosis, necrosis or cathepsin B-dependent cell death.

Parvovirus replication and oncolysis are stimulated by cellular changes associated with neoplastic transformation. It could be shown that H-1PV naturally displays antineoplastic activity against cell lines derived from human cervical carcinomas in both cell culture and animal models. These results underline the therapeutic potential of H-1PV against carcinomas. However, it should also be stated that parvoviruses fail, in certain cases, to completely eradicate the tumour or to stop its growth. Often resistant cells develop, leading to the possibility of tumor relapse. Moreover, although the virus preferentially replicates in tumor cells, it is also able to enter normal cells, reducing the amount of virus suitable for the treatment. Therefore, it would be of great advantage to reinforce their oncolytic activity and to find other agents that could act in concerto with parvovirus in killing cancer cells.

In summary, unfortunately, oncolytic viruses tested in humans when used in monotherapy protocols have shown a limited success in inducing on their own a complete and permanent eradication of the tumour. A fraction of tumour cells escape the viral treatment increasing the risk of tumor relapse. The fact that parvoviruses have been isolated from growing tumours indicate that alone these viruses are also not always potent enough to arrest the growth or cause the complete regression of neoplastic lesions. Therefore, it is highly desirable to find drugs that could act with the virus in efficiently killing cancer cells without additional harmful side effects. These agents could improve the outcome of the treatment by (i) killing by other means parvovirus-resistant cells, (ii) making cancer cells more susceptible to parvovirus cytotoxicity, therebay allowing reduction of the viral dose needed to achieve efficacy, and/or (iii) enabling the drugs to be used in lower concentrations, thereby improving safety.

Therefore, it is the object of the present invention to provide means for an improved parvovirus-based therapy.

According to the invention this is achieved by the subject matters defined in the claims. The present invention is based on the applicant's findings that by the combined treatment with a parvovirus and a histone deacetylase inhibitor (HDACI) the therapeutic efficiency could be synergistically improved. HDACIs are a structurally heterogeneous group of molecules. It was found that sub-lethal doses of HDACIs, namely sodium butyrate (NaB), trichostatin A (TSA), Valproic Acid (VPA) and suberoylanilide hydroxamic acid (SAHA) potentiate the antioneoplastic activity of parvoviruses in a synergistic manner in cancers, e.g. in cervical carcinoma derived HeLa (positive for HPV-18), CaSki and SiHa (positive for HPV-16) and primary cervical carcinoma cells as well as in pancreatic ductal adenocarcinoma (PDAC) derived AsPC-1 and Capan-1 cell lines. HDACIs reactivate the transcription of multiple genes which are silenced in cancer and by this means they are able to induce growth inhibition, differentiation and apoptosis of cancer cells. HDACI-treated cervical carcinoma cells as well as pancreatic ductal adenocarcinoma cells undergo apoptosis through an E2F-mediated process that correlates with the strong induction of the pro-apoptotic isoforms of the E2F-target gene p73, but does not rely on reactivation of p53. Furthermore, the non-structural protein (NS-1) of parvovirus is acetylated by HDACIs and consequently the replication and cell killing activities of the parvovirus is highly improved.

Thus, parvoviruses have tremendous therapeutic potential to treat cancers, e.g. prostate tumors, lung tumors, renal tumors, liver tumors, lymphoma, breast tumors, hepatoma or melanoma and in particular brain tumors, cervical carcinoma, or pancreatic carcinoma in combination with an HDCA inhibitor, preferably in a two step protocol.

In summary, it could be demonstrated that parvovirus H-1PV and HDAC inhibitors act synergistically in killing cancers, e.g. cervical carcinoma derived cell lines (HeLa, CaSki, SiHa) and primary tumour cells as well as pancreatic ductal adenocarcinoma (PDAC) derived cell lines (AsPC-1 and Capan-1). The cooperation between the two agents takes place using sub-lethal doses of HDAC inhibitors, which reduces the risk of unwanted side-effects for normal tissues. The combined therapy could allow the use of H-1PV (and other oncolytic parvoviruses) at lower concentrations without affecting its efficacy.

BRIEF DESCRIPTION OF THE DRAWINGS

(B) A summary of three independent experiments each performed in triplicate is presented. Bars represent mean values +/− relative standard deviations. P<0.05, paired Student's t tests are indicated (***).

Cervical cancer derived cell lines (HeLa, CaSki, SiHa) and non-established cervical cancer cell cultures (CxCa) were infected with H-1PV at the indicated MOIs (pfu/cell) and grown for 72 h in the presence (grey bars) or absence (white bars) of VPA (1 mM). After incubation, cell lysis was evaluated by measuring the release of lactate dehydrogenase (LDH). Hatched bars at the right hand side of each chart show the minimal dose of H-1PV able to kill 90-100% of the cancer cells as monotherapy. Similar cytotoxicity was obtained at lower viral MOIs, by combining H-1PV with a sub-lethal dose of VPA (1 mM), indicating that both agents synergistically cooperate in killing cancer cells.

$5 \times 10^6$ HeLa cells were subcutaneously injected in the right flank of 5 weeks-old female nude rats. After 5 days (when tumour reached the volume of 200-400 mm$^3$), tumour-bearing animals were randomized in four groups (n=8). Groups were treated either with DMEM (control), VPA (100 mk/kg), H-1PV (total dose of 1.25 109 pfu/animal, fractionated in 4 intratumoral administrations at days 5, 9, 16 and 23 post implantation), or a combination of both agents. Tumour volume was measured with a digital calliper on the days indicated and calculated according to the formula: volume (cm$^3$)=L×W×H (length L, cm; width W, cm; height H, cm). Data shown represents the average values with standard deviation bars.

APC-1 and Capan-1 cells were plated in 96 wells plates (2000 cells/well). After 16 hours, cell were infected with H-1PV at the indicated MOI and grown in the presence or absence of VPA for additional 72 hours. Cellular lysis was measured by LDH assay.

The present invention provides a pharmaceutical composition containing (a) a parvovirus and (b) a HDCA inhibitor, preferably as separate entities, e.g. in separate containers.

Preferably, in said pharmaceutical composition the parvovirus and the HDCA inhibitor are present in an effective dose and combined with a pharmaceutically acceptable carrier. "Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort.

An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art (see for example, Fingl et al., The Pharmocological Basis of Therapeutics, Goodman and Gilman, eds. Macmillan Publishing Co., New York, pp. 1-46 ((1975)).

Additional pharmaceutically compatible carriers can include gels, bioasorbable matrix materials, implantation elements containing the therapeutic agent, or any other suitable vehicle, delivery or dispensing means or material(s).

Administration of the compounds may be effected by different ways, e.g. by intravenous, intraperetoneal, subcutaneous, intramuscular, topical or intradermal administration. The route of administration, of course, depends on the kind of therapy and the kind of compounds contained in the pharmaceutical composition. A preferred route of administration is intravenous administration. The dosage regimen of the parvovirus and the HDACI is readily determinable within the skill of the art, by the attending physician based an patient data, observations and other clinical factors, including for example the patient's size, body surface area, age, sex, the particular parvovirus, HDACI etc. to be administered, the time and route of administration, the tumor type and characteristics, general health of the patient, and other drug therapies to which the patient is being subjected.

If the parvovirus in the combination of HDACIs according to the invention comprises infectious virus particles with the ability to penetrate through the blood-brain barrier, treatment can be performed or at least initiated by intravenous injection of the virus, e.g., H1 virus. A preferred route of administration is intratumoral administeration.

Since long-term intravenous treatment is susceptible to becoming inefficient as a result of the formation of neutralizing antibodies to the virus, different modes of administration can be adopted after an initial regimen intravenous viral administration, or such different administration techniques, e.g., intracranial or intratumoral virus administration, can be alternatively used throughout the entire course of parvoviral treatment.

As another specific administration technique, the parvovirus (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus composition to be injected locally at various times without further surgical intervention. The parvovirus or derived vectors can also be injected into the tumor by stereotactic surgical techniques or by neuronavigation targeting techniques.

Administration of the parvovirus can also be performed by continuous infusion of viral particles or fluids containing viral particles through implanted catheters at low flow rates using suitable pump systems, e.g., peristaltic infusion pumps or convection enhanced delivery (CED) pumps.

A yet another method of administration of the parvovirus composition is from an implanted article constructed and arranged to dispense the parvovirus to the desired cancer tissue. For example, wafers can be employed that have been impregnated with the parvovirus, e.g., parvovirus H1, wherein the wafer is attached to the edges of the resection cavity at the conclusion of surgical tumor removal. Multiple wafers can be employed in such therapeutic intervention. Cells that actively produce the parvovirus, e.g., parvovirus H1, or H1 vectors, can be injected into the tumor or into the tumoral cavity after tumor removal.

The combined therapy according to the invention is useful for the therapeutic treatment of cancers, e.g. prostate tumors, lung tumors, renal tumors, liver tumors, lymphoma, breast tumors, hepatoma or melanoma, in particular brain tumors, cervical carcinoma, or pancreatic carcinoma and can significantly improve the prognosis of said diseases. Parvovirus H1 infection effects killing of tumor cells but does not harm normal cells and such infection can, for example, be carried out by intracerebral use of a suitable parvovirus, e.g., parvovirus H1, or a related virus or vectors based on such viruses, to effect tumor-specific therapy without adverse neurological or other side effects.

The present invention also relates to the use of (a) a parvovirus and (b) an HDACI for the preparation of (a) pharmaceutical composition(s) for the treatment of cancer wherein, preferably, (a) and (b) are sequentially (or separately) administered.

In one preferred embodiment of the present invention, the combination of agents is utilized in the treatment of brain tumors such as glioma, medulloblastoma and meningioma, cervical carcinoma, or pancreatic carcinoma. Preferred gliomas are malignant human glioblastomas.

In another preferred embodiment of the present invention, the parvovirus of the composition includes parvovirus H1 (H-1PV) or a related parvovirus such as LuIII, Mouse minute virus (MMV), Mouse parvovirus (MPV), Rat minute virus (RMV), Rat parvovirus (RPV) or Rat virus (RV).

Patients treatable by the combination of agents according to the invention include humans as well as non-human animals. Examples of the latter include, without limitation, animals such as cows, sheep, pigs, horses, dogs, and cats.

HDACIs useful for the purposes of the present invention include all HDACIs that are effective in inhibiting tumor growth. The administration of an HDACI can be accomplished in a variety of ways (see above) including systemically by the parenteral and enteral routes. Preferably, the parvovirus and the HDACI are administered as separate compounds. The preferred period of time between administration of the HDACI and the parvovirus is from −30 (administration of HDACI before the treatment with parvovirus) to 60 days after the treatment with parvovirus. Concomitant treatment with the two agents is also possible.

Particular examples of HDCAIs suitable for the combined therapy include sodium butyrate (NaB), trichostatin A (TSA), suberoylanilide hydroxamic acid (SAHA) or valproic acid (VPA).

The below examples explain the invention in more detail.

EXAMPLE 1

Materials and Methods (A) HDAC Inhibitors

Sodium butyrate (NaB) and trichostatin A (TSA) were purchased from SIGMA-Aldrich (Munich, Germany), suberoylanilide hydroxamic acid (SAHA) and valproic acid (VPA) from Alexis Biochemicals (Enzo Life Science, Lorrach, Germany).

(B) Lactate-Dehydrogenase Assay (LDH)

Parvovirus cytotoxicity was measured by evaluating the release of lactate dehydrogenase in the medium using the CytoTox 96 kit from Promega (Mannheim, Germany). The day before infection, 2000 cells were seeded per well in 96-well plate in 50 µl of culture medium. After 24 hours, cells were infected with 50 µl of serum-free medium containing H-1PV or treated with HDAC inhibitors in 7 replicates per condition. The day of measurement, 3 out of 7 wells were incubated for 30 minutes with lysis buffer to estimate the maximum LDH release under conditions of 100% lysis. Afterwards, the plate was centrifuged and 50 µl of supernatant were mixed with the substrate mix. The LDH enzyme catalyzes a colorimetric reaction that is indicative of the amount of enzyme released in the medium. After 30 minutes, the reaction was stopped and analyzed using the Elisa reader MultiScan at 492 nm.

(C) Determination of the Sub-G1 Cell Population

Virus infected or drug-treated cells were harvested from culture dishes with 0.05% Trypsin-EDTA solution, collected in a Falcon tube and then washed twice with PBS. Cells were then resuspended in 260 µl of PBS, fixed with 700 µl of cold 100% ethanol added drop wise under vortexing, and stored at 4° C. overnight. After two washes in PBS, the cell pellet was resuspended in a PBS solution containing 20 µg/ml of RNase and 10 µg/ml of propidium iodide (Sigma). Cell suspension was filtered and analyzed by FACSort flow cytometer (Becton-Dickinson). A minimum of 20,000 events were acquired and then analyzed with the CellQuest software (Becton-Dickinson) (San Jose, Calif.).

EXAMPLE 2

Parvovirus H-1PV and HDAC Inhibitors Act Synergistically in Killing Cervical Carcinoma Derived Cell Lines (HeLa, CaSki, SiHa) and Primary Tumor Cells It was found that sub-lethal doses of HDACIs, namely sodium butyrate (NaB), trichostatin A (TSA) and suberoylanilide hydroxamic acid (SAHA) increase PV cytotoxicity in a synergistic manner in cervical carcinoma derived HeLa (positive for HPV-18), CaSki and SiHa (positive for HPV-16) and primary cervical cancer cells.

Figure 1:
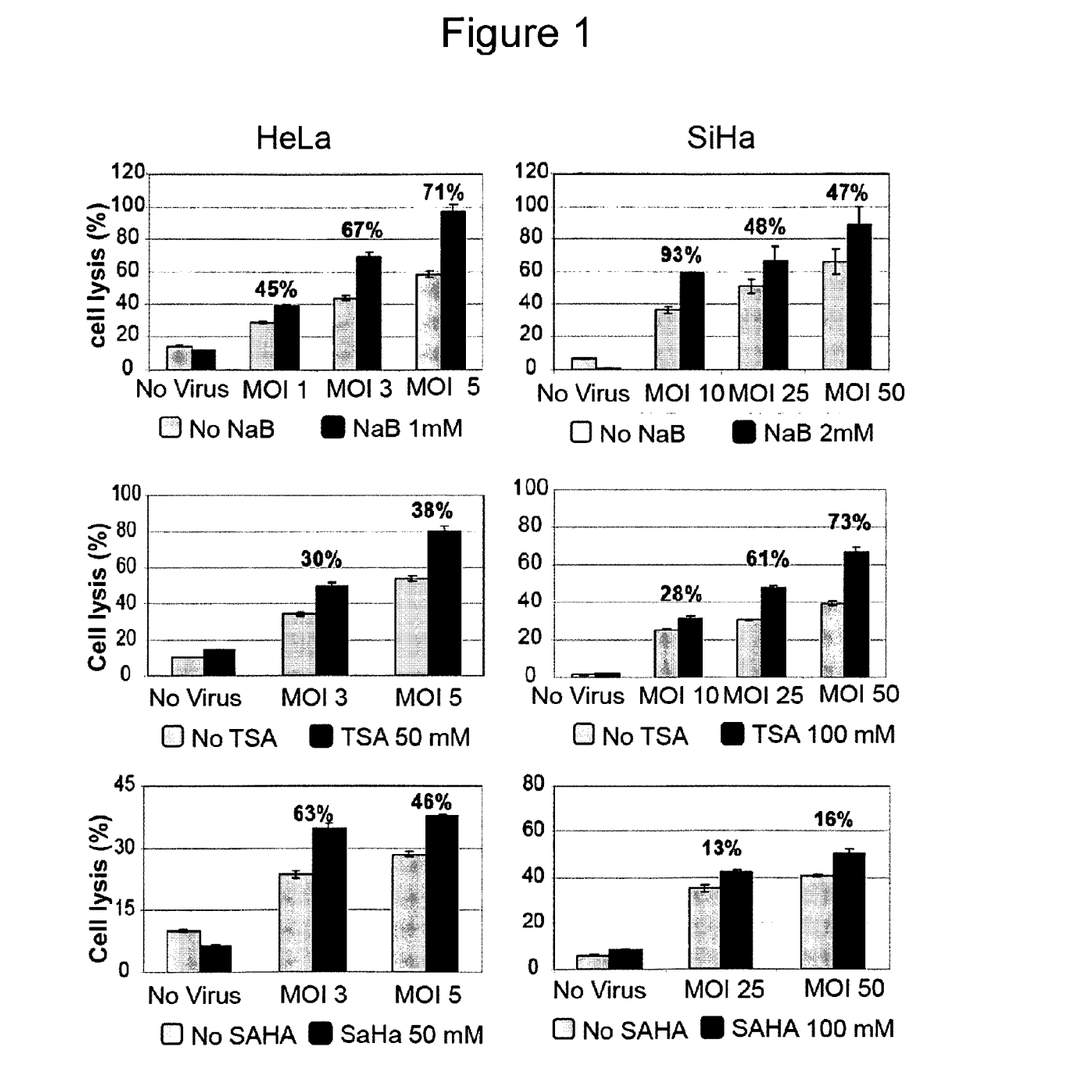
FIG. 1: H-1PV and HDAC inhibitors kill cervical carcinoma derived cell lines in a synergistic manner HeLa (HPV 18 positive cell line) and SiHa (HPV 16 positive) were infected with H-1PV at the indicated MOIs and subsequently grown in the presence (black bar) or absence (grey bar) of HDACIs. The HDACIs tested were NaB (1 mM), TSA (50 nM) and SAHA (50 nM) for HeLa and NaB (2 mM), TSA (100 nM) and SAHA (500 nM) for SiHa cells. After incubation cell lysis was evaluated by measuring the release of lactate dehydrogenase (LDH). The values above bars (expressed in %) indicate synergistic effects obtained. Results from one representative experiment are shown.
Figure 2:
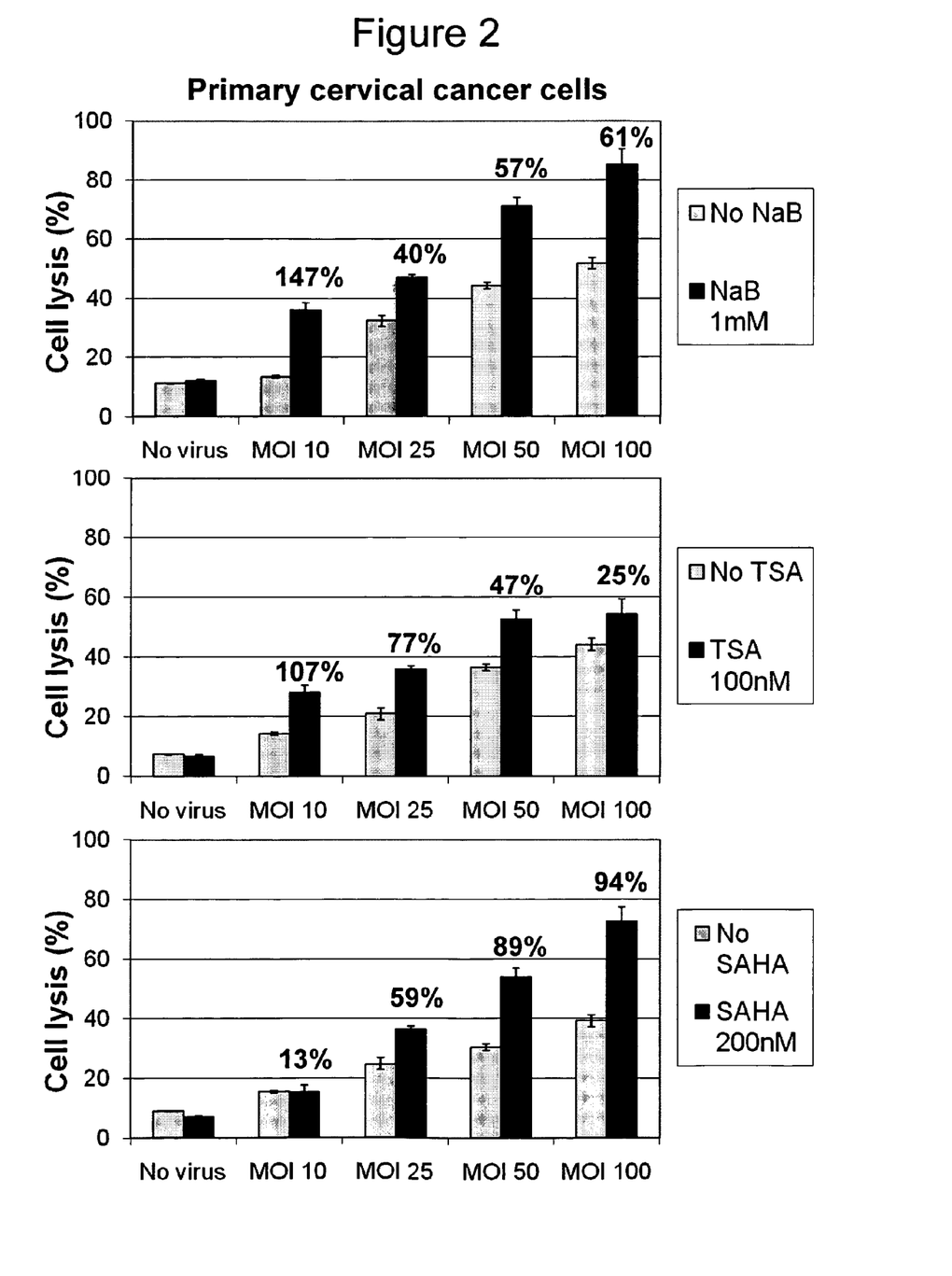
FIG. 2: H-1PV and HDAC inhibitors kill cervical carcinoma derived cells in a synergistic manner Primary cervical cancer cells were infected with H-1PV at the indicated MOIs and subsequently grown in the presence (black bar) or absence (grey bar) of HDACIs. The HDACIs tested were NaB (1 mM), TSA (100 nM) and SAHA (200 nM). After incubation, cell lysis was evaluated by measuring the release of lactate dehydrogenase (LDH). The values (%) indicate synergistic effects obtained. Results from one representative experiment are shown.

FIG. 1 shows the results obtained from LDH assays in HeLa and SiHa cells using various H-1PV multiplicities of infection (MOI=pfu/cell) in combination with the three HDACIs tested. Similar results were also obtained in CaSki cells (data not shown) and primary cervical cancer cells (CxCa) (FIG. 2) where a synergistic effect of up to 94%, resulting in approximately 80% cell death was achieved by combining SAHA (200 nM) with H-1PV (MOI=100 pfu/cell). Synergistic effects in killing the cancer cells above mentioned, were also observed using parvovirus in combination with another HDACI, namely VPA (data not shown).

Figure 3:
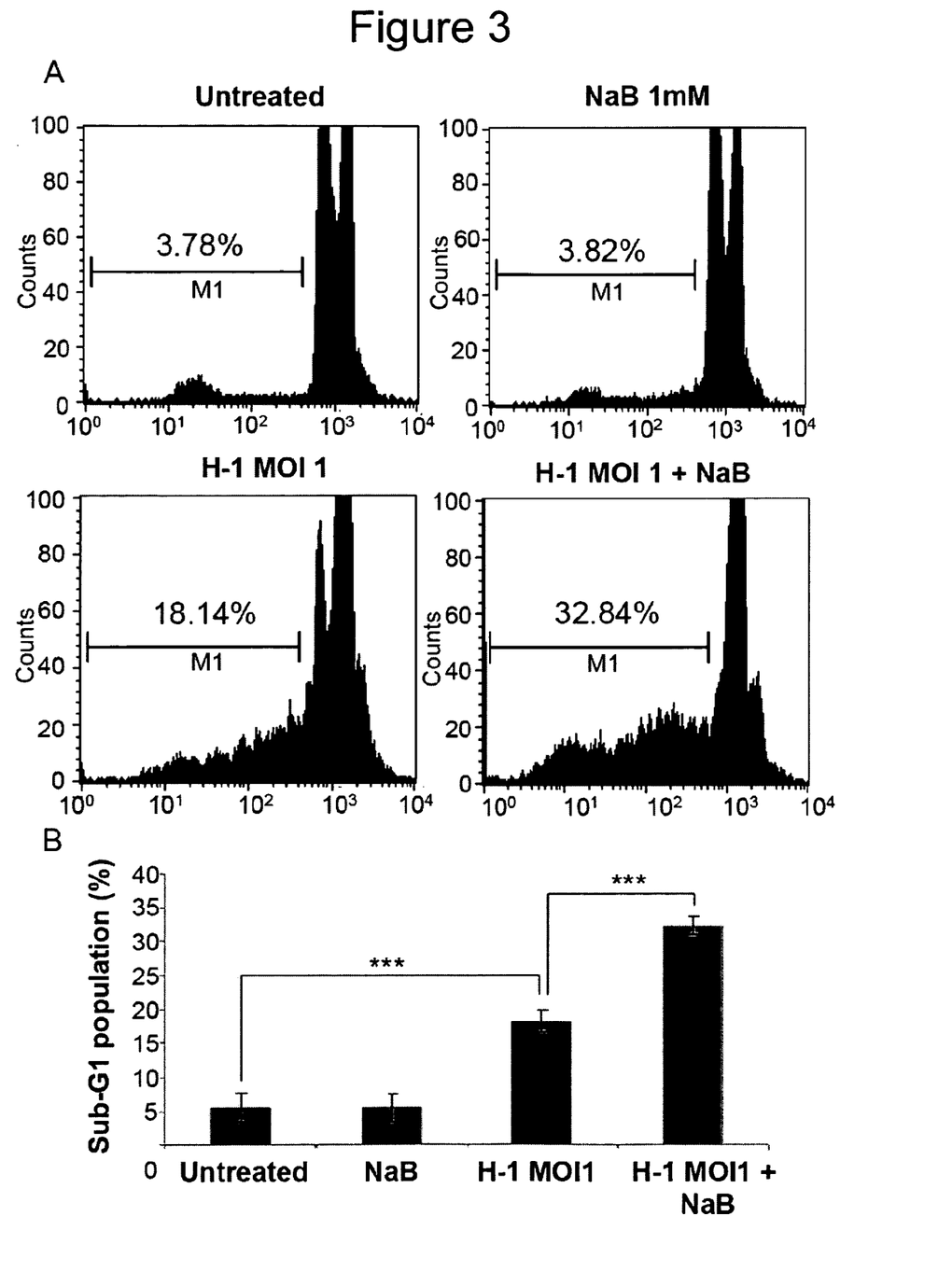
FIG. 3: HDAC inhibitors enhance H-1 PV cytotoxicity (A) Either mock treated or H-1PV (MOI: 1 pfu/cell) infected HeLa cells were grown in the presence or absence of NaB (1 mM). After 48 h, cells were collected for the analysis of sub-G1 cell population by flow cytometry. The co-treatment with NaB increases the sub-GI cell population induced by H-1PV, indicating that the compound acts synergistically with the virus in killing cancer cells.

The synergistic effect in killing cancer cells between H-1PV and HDACIs was confirmed by flow cytometry in HeLa and CxCa, analyzing the fraction of cells containing less than 2N DNA content (sub-G1 cell population), as a marker of DNA fragmentation, a common feature of cells undergoing apoptosis. FIG. 3 shows the results obtained in HeLa cells. H-1PV infection is associated with an increase of the apoptotic sub-G1 cell population that is further enhanced by the addition of NaB (from 18% to 32%).

Figure 4:
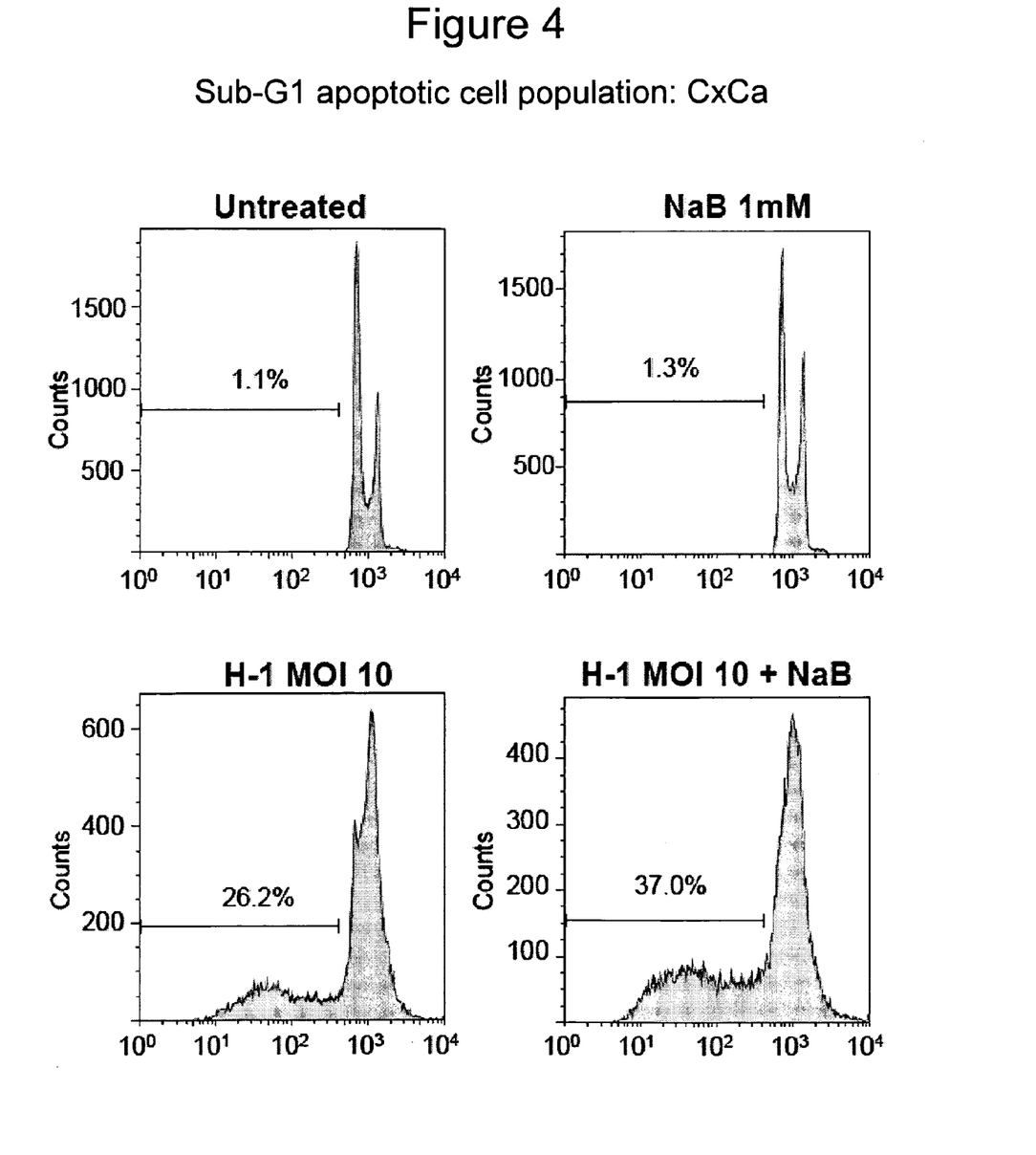
FIG. 4: H-1PV/HDAC inhibitors co-treatment increases the fraction of cells undergoing apoptosis The increase of the sub-G1 cell population, labeled as a blue line and indicated by numbers, indicates that HDAC inhibitors enhance H-1PV cytotoxic properties.

FIG. 4 shows the results obtained in primary cervical cancer cells. H-1PV and HDAC inhibitors act synergistically in killing CxCa cells as demonstrated by the increase of apoptosis (from 26 to 37%). The conditions, in which H-1PV/HDACIs combinations give the highest synergistic effect in killing cervical carcinoma derived cells are summarized in Table 1.

TABLE 1

Conditions under which H-1PV and HDACIs combinations show the highest synergistic effect in killing cervical cancer cells

| Cell line | H-1PV + [NaB] | | | H-1PV + [TSA] | | | H-1PV + [SAHA] | | |
| --- | --- | --- | --- | --- | --- | --- | --- | --- | --- |
| | MOI | mM | % synergy, (% killed cells) | MOI | nM | % synergy, (% killed cells) | MOI | nM | % synergy, (% killed cells) |
| HeLa | 5 | 1 | 71 (97) | 10 | 20 | 50 (80) | 10 | 100 | 26 (60) |
| SiHa | 25 | 2 | 68 (80) | 50 | 20 | 75 (83) | 10 | 100 | 38 (57) |
| Primary cervical cancer cells | 100 | 1 | 87 (85) | 50 | 100 | 47 (52) | 100 | 200 | 94 (72) |

EXAMPLE 3

Parvovirus H-1PV and HDAC Inhibitors Act Synergistically In Vitro (a) and In Vivo (b) in Killing Cervical Carcinoma Derived Cell Lines and Primary Tumor Cells (a) In Vitro Synergism.

It was found that sub-lethal doses of HDACIs, namely Valproic acid (VPA), sodium butyrate (NaB), trichostatin A (TSA) and suberoylanilide hydroxamic acid (SAHA) potentiate H-1PV cytotoxicity in a synergistic manner in cervical carcinoma cell lines HeLa, positive for HPV-18, CaSki and SiHa, transformed by HPV-16 and low passage cervical carcinoma cell cultures.

Figure 5:
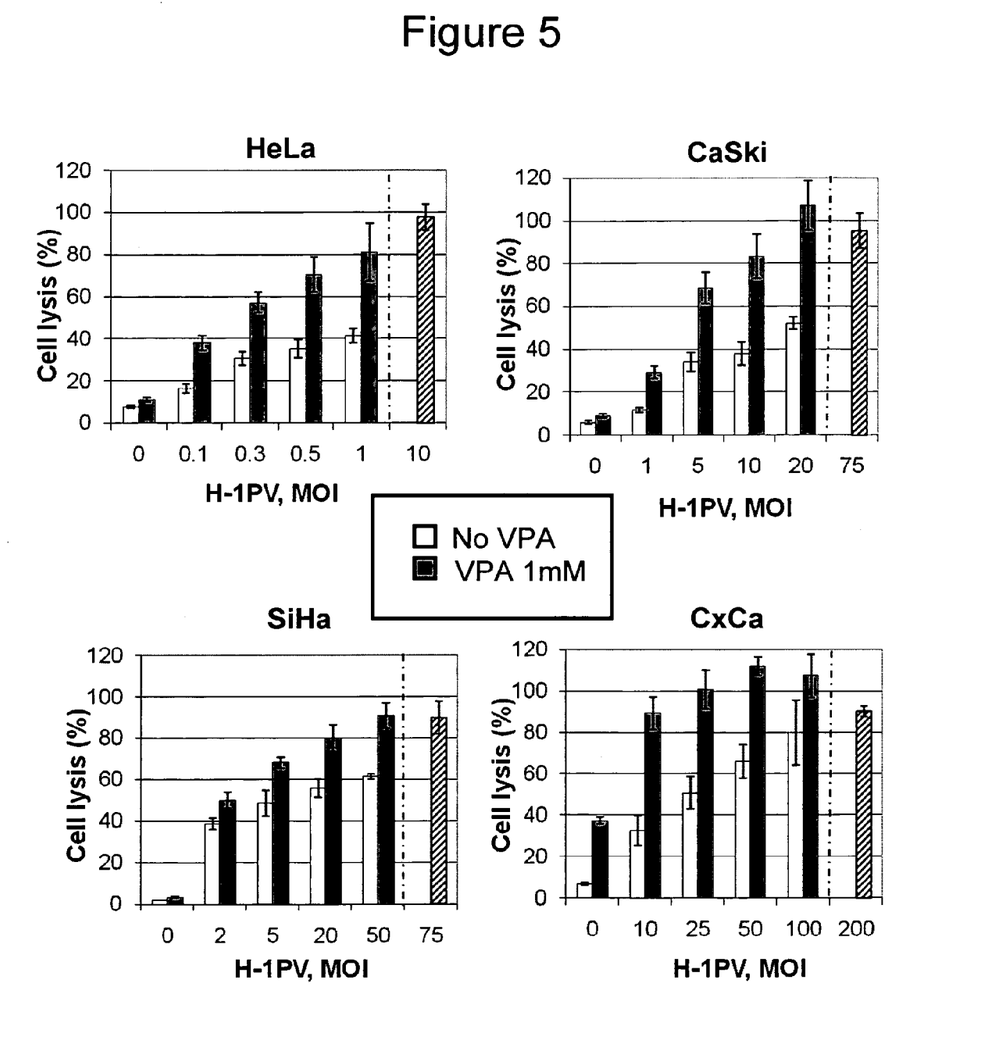
FIG. 5: H-1PV and HDAC inhibitors kill cervical carcinoma derived cell lines in a synergistic manner.

FIG. 5 shows the results obtained from LDH assays (which measure the release of lactate dehydrogenase in the medium, as an indicator of cell lysis) using H-1PV at various multiplicities of infection (MOI, expressed in plaque-forming units [pfu] per cell) in combination with 1 mM VPA. When applied singly, VPA did not have any significant effect on cellular growth at the concentration used, while the parvovirus killed all the cervical carcinoma cell cultures in a MOI-dependent fashion. The sub-lethal dose of VPA boosted parvovirus-induced cell killing in a synergistic manner, increasing by up to 50-100%. Confirmation of these results was obtained by flow cytometric determination of the apoptotic sub-G1 cell population (data not shown). Similar results were also obtained combining H-1PV with NaB, TSA or SaHa (Table 2).

TABLE 2

Conditions under which H-1PV and HDACIs combinations show the highest synergistic effect in killing cervical cancer cells.

| Cell lines | [NaB] + H-1PV | | | [SAHA] + H-1PV | | | [TSA] + H-1PV | | |
|---|---|---|---|---|---|---|---|---|---|
| | mM | MOI | Synergy * | nM | MOI | Synergy * | nM | MOI | Synergy * |
| HeLa | 1 | 1 | 78 (51) | 50 | 3 | 63 (34) | 50 | 3 | 46 (51) |
| | 1 | 3 | 68 (79) | 50 | 5 | 45 (37) | 50 | 5 | 37 (56) |
| | 1 | 5 | 71 (97) | 50 | 10 | 27 (60) | 50 | 10 | 45 (88) |
| CaSki | 0.5 | 2 | 43 (54) | 100 | 5 | 43 (61) | 50 | 2 | 75 (45) |
| | 0.5 | 5 | 48 (77) | 100 | 10 | 39 (85) | 50 | 5 | 77 (73) |
| | 0.5 | 10 | 49 (91) | 100 | 20 | 49 (100) | 50 | 10 | 82 (96) |
| SiHa | 2 | 10 | 94 (59) | | N.A. | | 100 | 10 | 46 (40) |
| | 2 | 25 | 48 (67) | | N.A. | | 100 | 25 | 92 (76) |
| | 2 | 50 | 47 (89) | | N.A. | | 100 | 50 | 89 (82) |
| CxCa | 1 | 10 | 50 (55) | 200 | 10 | 105 (26) | 100 | 10 | 107 (28) |
| | 1 | 25 | 61 (70) | 200 | 25 | 90 (53) | 100 | 25 | 77 (36) |
| | 1 | 50 | 111 (100) | 200 | 50 | 95 (73) | 100 | 50 | 47 (53) |

* Synergy is expressed as % increase in virus-induced killing. Number in brackets indicate percentages of killed cells. At the concentration used, the HDACIs had no or little effect on tumour cell growth when applied singly.

(b) In Vivo Synergism

Figure 6:
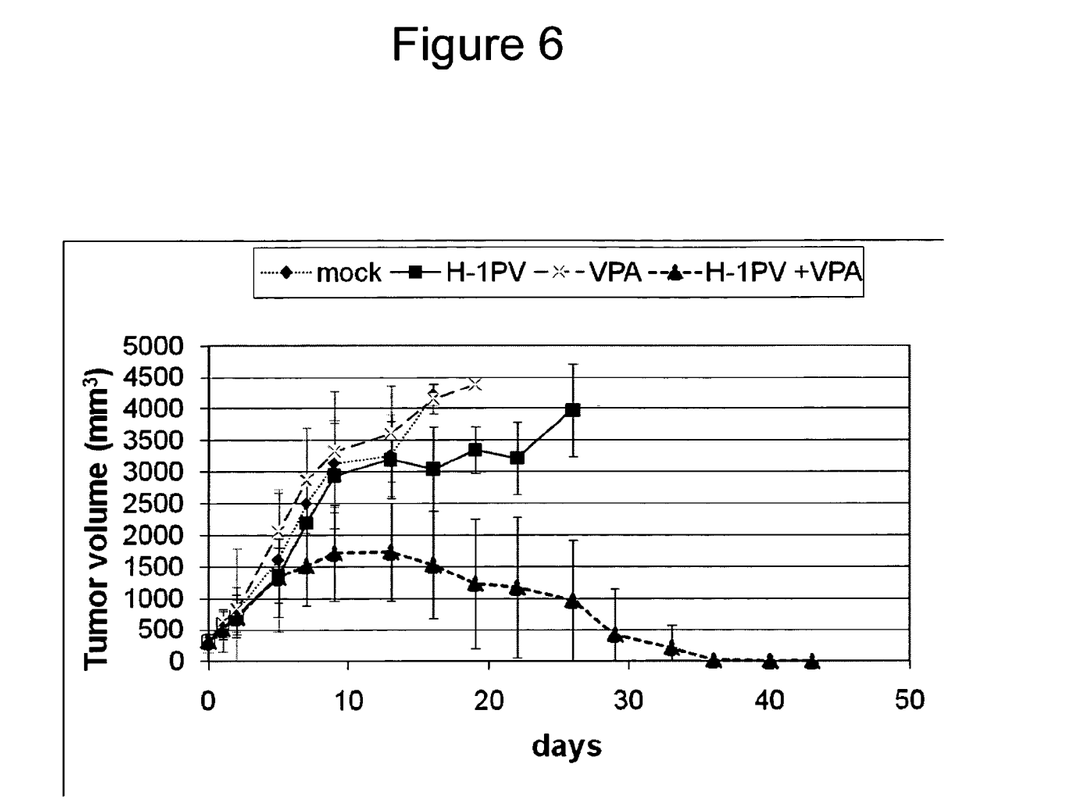
FIG. 6: H-1PV/VPA co-treatment leads to complete regression of HeLa established tumors.

In order to validate the H-1PV/HDACIs synergism in vivo, a HeLa xenograft nude rat model was used. H-1PV alone was able to achieve the full regression of established tumours, when a high virus dose was administrated ($2.5 \times 10^9$ pfu/animal, fractioned in 4 intratumoral administration at weekly interval (data not shown). At a lower virus dose of $1.25 \times 10^9$ (pfu/animal, fractionated as above) tumour growth slowed down but non regression took place, indicating that a critical dose of the virus is required in order to have a therapeutic effect. At the concentration of 100 mg/kg, VPA failed to impair tumour growth which was comparable to mock-treated controls (rats were sacrificed when tumours reached the maximum tolerable size of 5 cm³). In contrast, tumour growth was strikingly reduced and eventually arrested at the size of 1-3.2 cm³, if animals injected with the lower viral dose were co-treated with VPA. Most remarkably, this stabilization was followed by a rapid regression leading to the complete disappearance of pre-existing tumours in all co-treated animals (FIG. 6). No loss of weight or other adverse side effects were documented in any of the treated animals. These results further strengthen the concept of combining H-1PV and HDACIs for the treatment of cervical carcinomas.

EXAMPLE 4

Parvovirus H-1PV and HDAC Inhibitors Act Synergistically in Killing Pancreatic Ductal Adenocarcinoma (PDAC) Derived Cell Lines (APC-1 and Capan-1)

In Vitro Synergism.

It was found that sub-lethal doses of HDACIs, namely Valproic acid (VPA) increase PV cytotoxicity in a synergistic manner in pancreatic ducal adenocarcinoma (PDAC) derived AP-1 and Capan-1 cell lines.

Figure 7:
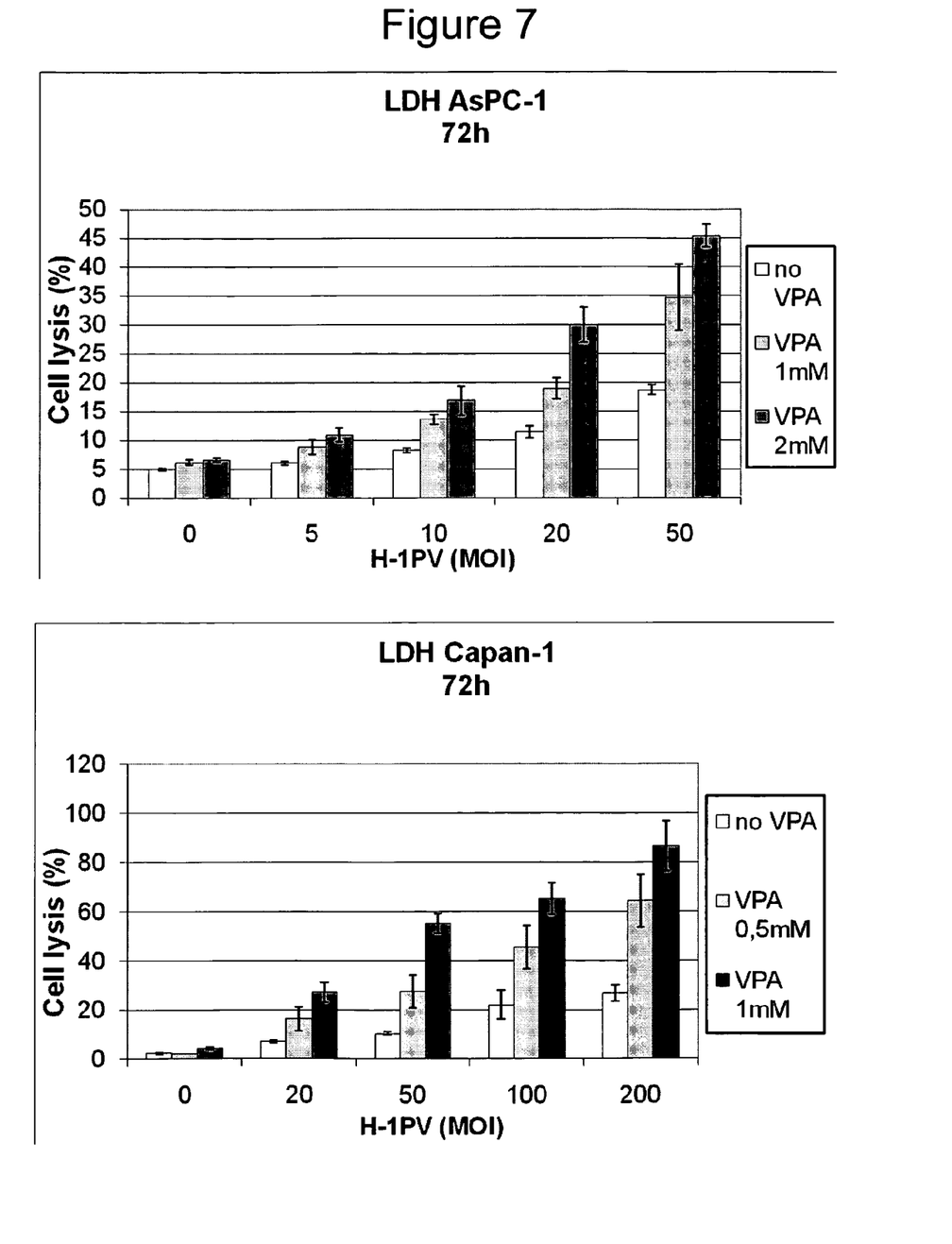
FIG. 7: H-1PV and HDAC inhibitors kill PDAC derived cells in a synergistic manner.

FIG. 7 shows the results obtained from LDH assays in AP-1 and Capan-1 cell lines that have been described to be quite resistant to PV cytotoxicity (Dempe et al., 2010). Cells were seeded in 96 wells plate and then infected with various concentrations of H-1PV in the presence or absence of the HDACI Valproic acid (VPA). After 72 hours cell lysis was measured by LDH assay. As shown in FIG. 7, at the concentrations used for the experiments, single treatment with VPA had no effect on the growth of both cell lines. Consistent with previous results, H-1PV displayed only a limited cytotoxicity against these cultures, even after infection at high multiplicities. The cytotoxic activity of H-1PV was strikingly enhanced by VPA. These results further support combining HDACIs and H-1PV for the treatment of various tumour entities.

LIST OF REFERENCES

Dempe S, Stroh-Dege A Y, Schwarz E, Rommelaere J, Dinsart C. (2010) SMAD4: a predictive marker of PDAC cell permissiveness for oncolytic infection with parvovirus H-1PV. *Int J Cancer* 126: 2914-27.

The invention claimed is:

1. A method of treating cervical carcinoma or pancreatic carcinoma comprising the administration of an effective dose of a pharmaceutical composition containing (a) a H-1 parvovirus (H-1PV) and (b) a histone deacetylase inhibitor (HDACI) selected from the group consisting of valproic acid (VPA) and suberoylanilide hydroxamic acid (SAHA), wherein said effective dose comprises an amount sufficient to lead to the reduction or remission of said cervical carcinoma or pancreatic carcinoma, wherein (a) the H-1 parvovirus (H-1PV) and (b) the HDACI are sequentially administered.

2. The method of claim 1, wherein the H-1 parvovirus (H-1PV) (a) is administered prior to the HDACI (b).

3. The method of claim 1, wherein said H-1 parvovirus (H-1PV) is administered by intratumoral administration.